United States Patent [19]

Yamamoto et al.

[11] Patent Number: 4,784,474

[45] Date of Patent: Nov. 15, 1988

[54] SPIRO-OXAZINE COMPOUNDS AND PREPARATION THEREOF AND PHOTOCHROMIC SHAPED ARTICLE

[75] Inventors: Shinichi Yamamoto, Kyoto; Takashi Taniguchi, Shiga, both of Japan

[73] Assignee: Toray Industries, Inc., Tokyo, Japan

[21] Appl. No.: 81,587

[22] Filed: Aug. 3, 1987

Related U.S. Application Data

[63] Continuation of Ser. No. 750,007, Jun. 27, 1985, abandoned.

[30] Foreign Application Priority Data

Jul. 6, 1984 [JP]  Japan ................... 59-139266
Aug. 24, 1984 [JP] Japan ................... 59-175048

[51] Int. Cl.$^4$ ................... G02B 5/23; G02B 13/14; C07D 273/00
[52] U.S. Cl. ................... 350/354; 252/586; 544/70; 544/71; 430/345; 350/438
[58] Field of Search ................... 252/586; 350/354, 438; 544/70, 71; 430/345

[56] References Cited

U.S. PATENT DOCUMENTS

| | | | |
|---|---|---|---|
| 3,562,172 | 2/1971 | Ono et al. | 252/586 |
| 3,578,602 | 5/1971 | Ono et al. | 252/586 |
| 3,843,550 | 10/1974 | Hinnen | 252/586 |
| 4,215,010 | 7/1980 | Hovey | 252/586 |

FOREIGN PATENT DOCUMENTS

| | | |
|---|---|---|
| 659801 | 8/1965 | Belgium . |
| 1927849 | 12/1970 | Fed. Rep. of Germany . |
| 49-53180 | 5/1974 | Japan . |
| 1227713 | 4/1971 | United Kingdom . |
| 2117390 | 10/1983 | United Kingdom . |

OTHER PUBLICATIONS

Arnold et al., "Spektroskopische ...", tetrahedron, vol. 27, pp. 1699–1713, 1971.
G. H. Brown: Techniques of Chemistry, vol. III, Photochromism pp. 49–105, 1971, published by Wiley & Sons, Inc.

Primary Examiner—Matthew A. Thexton
Assistant Examiner—Catherine S. Kilby
Attorney, Agent, or Firm—Austin R. Miller

[57] ABSTRACT

A novel spiro-oxazine compound of the formula (A):

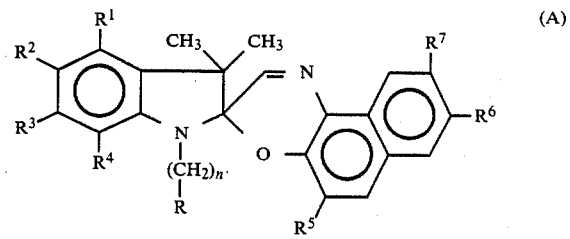

wherein $R^1$, $R^2$, $R^3$, $R^4$, $R^5$, $R^6$ and $R^7$ independently represent hydrogen, (C1 or 2) alkyl, halogenated (C1 or 2) alkyl, (C1 or 2) alkoxy, halogen or nitro, R is unsubstituted or substituted phenyl or naphthyl, and n is 1 to 5.

The spiro-oxazine compound is prepared by reacting a precursor of the spiro-oxazine compound of the formula (A), which has a substituent of the formula: —(CH$_2$)$_n$R in the nitrogen atom of the indoline nucleus, with an α-nitroso-β-naphthol. The spiro-oxazine compound is valuable as a photochromic material and exhibits enhanced fatigue resistance in photocolorability.

13 Claims, No Drawings

SPIRO-OXAZINE COMPOUNDS AND PREPARATION THEREOF AND PHOTOCHROMIC SHAPED ARTICLE

This application is a continuation of application Ser. No. 750,007, filed June 27, 1985, now abandoned.

BACKGROUND OF THE INVENTION (1) Field of the Invention

The present invention relates to a novel spiro-oxazine compound which is valuable as a photochromic material for printing and photography, a photochromic material for optical devices, a photochromic material for recording media and a photochromic material for clothings and decorative articles (2) Description of the Related Art As a typical instance of photochromic compounds, there can be mentioned a spiropyran compound, and there are known a variety of compounds of this type [G.H. Brown, "Photochromism", Wiley Interscience, New York (1971)].

As the photochromic spiro-oxazine compound, 1,3,3-trimethylspiro [indoline-2,3'-[3H]-naphtho[2,1-b](1,4)-oxazine] and substituent derivatives thereof are disclosed in U.S. Pat. Nos. 3,578,602, 3,562,172 and 4,215,010 and Japanese Unexamined Patent Publication No. 48-23787.

Spiropyran compounds exhibit poor fatigue resistance when used repeatedly for coloration and decolorization. The known spiro-oxazine compounds have improved fatigue resistance over the spiropyran compounds, but coloration by exposure to light or by irradiation is limited to blue. Both of them are at least partially decomposed to non-photochromic compounds or colored compounds when they are brought into contact with an acid substance.

SUMMARY OF THE INVENTION

The primary object of the present invention is to provide a novel class of photochromic spiro-oxazine compounds which do not have the above-mentioned defects of the known photochromic compounds, i.e., exhibit enhanced fatigue resistance in photocolorability.

In one aspect of the present invention, there is provided spiro-oxazine compound represented by the following general formula (A):

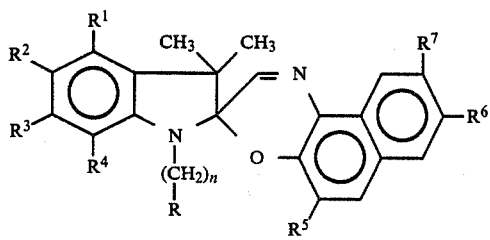
(A)

wherein $R^1$, $R^2$, $R^3$, $R^4$, $R^5$, $R^6$ and $R^7$ independently represent a hydrogen atom or a substituent selected from the group consisting of an alkyl group having 1 or 2 carbon atoms, a halogenated alkyl group having 1 or 2 carbon atoms, an alkoxy group having 1 or 2 carbon atoms, a halogen atom such as fluorine, chlorine or bromine, and a nitro group, R represents an unsubstituted or substituted phenyl or naphthyl group, and n is an integer of from 1 to 5.

In another aspect of the present invention, there is provided a method for preparing the spiro-oxazine compound of the above-mentioned formula (A), which comprises reacting a precursor of the spiro-oxazine compound of the formula (A), which has a substituent of the formula: $-(CH_2)_n R$ (R is the same as defined above) in the nitrogen atom of the indoline nucleus, with an α-nitroso-β-naphthol represented by the following formula:

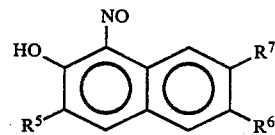

wherein $R^5$, $R^6$ and $R^7$ are the same as defined above.

In still another aspect of the present invention, there is provided a shaped article comprising an optically transparent material and the spiro-oxazine compound of the formula (A).

DESCRIPTION OF THE PREFERRED EMBODIMENTS

As specific examples of the substituent included in the substituted phenyl or naphthyl group "R" in the spiro-oxazine compound represented by the general formula (A), there can be mentioned a hydroxyl grop; an amino group; organic substituted amino group such as methylamino and diethylamino groups; lower alkoxy groups having 1 to 4 carbon atoms such as methoxy, ethoxy and t-butoxy groups; aralkoxy groups having 7 to 15 carbon atoms such as a benzyloxy group; aryloxy groups having 6 to 14 carbon atoms such as a phenoxy group; alkyl groups having 1 to 4 carbon atoms such as methyl, ethyl and t-butyl groups; halogen atoms such as flourine, chlorine and bromine; a cyano group; a carboxyl group; alkoxycarbonyl groups having 2 to 5 carbon atoms such as an ethoxycarbonyl group; acyl groups having 2 to 11 carbon atoms such as acetyl and benzoyl groups; trihalomethyl groups such as a trifluoromethyl group; and a nitro group. The substituent is not limited to a monosubstituent but includes a polysubstituent having at least two substituent groups which may be the same or different. The position of the substituent included in R should be changed according to the intended object and use and the kind of the substituent. In order to quicken the photochromic response, when R is a phenyl group, introduction of substituents at the meta-position is especially preferable. In order to increase the coloration density by irradiation at room temperature, a spiro-oxazine compound in which R is a naphthyl group or a phenyl group having at least 2 substituents is especially preferable. In order to shift the absorption wave length to shorter, a spiro-oxazine compound in which R has at least one electron withdrawing substituent is especially preferable.

In the above general formula (A), n may be an integer of from 1 to 5. However, a compound in which n is 1 is preferable for manifesting the electronic effect of the substituent and controlling the absorption wavelength for coloration.

The substituents $R^1$, $R^2$, $R^3$, $R^4$, $R^5$, $R^6$ and $R^7$ in the general formula (A) may be the same or different.

The spiro-oxazine compounds represented by the general formula (A) include, for example, the following derivatives of spiro [indoline-2,3'-[3H]-naphtho[2,1-b](1,4)-oxazine[, and spiro-oxazine compounds corresponding to these derivatives in which $R^1$, $R^2$, $R^3$, $R^4$, $R^5$, $R^6$, and $R^7$, which may be the same or different, represent a hydrogen atom or a substituent selected from a methyl group, an ethyl group, a methoxy group, an ethoxy group, a fluoro group, a chloro group, a bromo group and a nitro group:

1-benzyl-3,3-dimethyl derivative,
1-(2-hydroxybenzyl)-3,3-dimethyl derivative,
1-(3-hydroxybenzyl)-3,3-dimethyl derivative,
1-(4-hydroxybenzyl)-3,3-dimethyl derivative,
1-(2-aminobenzyl)-3,3-dimethyl derivative,
1-(3-aminobenzyl)-3,3-dimethyl derivative,
1-(4-aminobenzyl)-3,3-dimethyl derivative,
1-(2-methylaminobenzyl)-3,3-dimethyl derivative,
1-(3-methylaminobenzyl)-3,3-dimethyl derivative,
1-(4-methylaminobenzyl)-3,3-dimethyl derivative,
1-(2-dimethylaminobenzyl)-3,3-dimethyl derivative,
1-(3-dimethylaminobenzyl)-3,3-dimethyl derivative,
1-(4-dimethylaminobenzyl)-3,3-dimethyl derivative,
1-(2-diethylaminobenzyl)-3,3-dimethyl derivative,
1-(3-diethylaminobenzyl)-3,3-dimethyl derivative,
1-(4-diethylaminobenzyl)-3,3-dimethyl derivative,
1-(2-methoxybenzyl)-3,3-dimethyl derivative,
1-(3-methoxybenzyl)-3,3-dimethyl derivative,
1-(4-methoxybenzyl)-3,3-dimethyl derivative,
1-(2,3-dimethoxybenzyl)-3,3-dimethyl derivative,
1-(2,4-dimethoxybenzyl)-3,3-dimethyl derivative,
1-(2,5-dimethoxybenzyl)-3,3-dimethyl derivative,
1-(2,6-dimethoxybenzyl)-3,3-dimethyl derivative,
1-(3,4-dimethoxybenzyl)-3,3-dimethyl derivative,
1-(3,5-dimethoxybenzyl)-3,3-dimethyl derivative,
1-(2,3,4-trimethoxybenzyl)-3,3-dimethyl derivative,
1-(2,3,5-trimethoxybenzyl)-3,3-dimethyl derivative,
1-(2,3,6-trimethoxybenzyl)-3,3-dimethyl derivative,
1-(2,4,5-trimethoxybenzyl)-3,3-dimethyl derivative,
1-(2,4,6-trimethoxybenzyl)-3,3-dimethyl derivative,
1-(3,4,5-trimethoxybenzyl)-3,3-dimethyl derivative,
1-(2,3,4,5-tetramethoxybenzyl)-3,3-dimethyl derivative,
1-(2,3,4,6-tetramethoxybenzyl)-3,3-dimethyl derivative,
1-(2,3,5,6-tetramethoxybenzyl)-3,3-dimethyl derivative,
1-(2,3,4,5,6-pentamethoxybenzyl)-3,3-dimethyl derivative,
1-(2-ethoxybenzyl)-3,3-dimethyl derivative, 1-(3-ethoxylbenzyl)-3,3-dimethyl derivative,
1-(4-ethoxybenzyl)-3,3-dimethyl derivative,
1-(2,3-diethoxybenzyl)-3,3-dimethyl derivative,
1-(2,4-diethoxybenzyl)-3,3-dimethyl derivative,
1-(2,5-diethoxybenzyl)-3,3-dimethyl derivative,
1-(2,6-diethoxybenzyl)-3,3-dimethyl derivative,
1-(3,4-diethoxybenzyl)-3,3-dimethyl derivative,
1-(3,5-diethoxybenzyl)-3,3-dimethyl derivative,
1-(2-t-butoxybenzyl)-3,3-dimethyl derivative,
1-(3-t-butoxybenzyl)-3,3-dimethyl derivative,
1-(4-t-butoxybenzyl)-3,3-dimethyl derivative,
1-(2-benzyloxybenzyl)-3,3-dimethyl derivative,
1-(3-benzyloxybenzyl)-3,3-dimethyl derivative,
1-(4-benzyloxybenzyl)-3,3-dimethyl derivative,
1-(2,3-dibenzyloxybenzyl)-3,3-dimethyl derivative,
1-(2,4-dibenzyloxybenzyl)-3,3-dimethyl derivative,
1-(2,5-dibenzyloxybenzyl)-3,3-dimethyl derivative,
1-(2,6-dibenzyloxybenzyl)-3,3-dimethyl derivative,
1-(3,4-dibenzyloxybenzyl)-3,3-dimethyl derivative,
1-(3,5-dibenzyloxybenzyl)-3,3-dimethyl derivative,
1-(2,3,4-tribenzyloxybenzyl)-3,3-dimethyl derivative,
1-(2,3,5-tribenzyloxybenzyl)-3,3-dimethyl derivative,
1-(2,3,6-tribenzyloxybenzyl)-3,3-dimethyl derivative,
1-(2,4,5-tribenzyloxybenzyl)-3,3-dimethyl derivative,
1-(2,4,6-tribenzyloxybenzyl)-3,3-dimethyl derivative,
1-(3,4,5-tribenzyloxybenzyl)-3,3-dimethyl derivative,
1-(2-phenoxybenzyl)-3,3-dimethyl derivative,
1-(3-phenoxybenzyl)-3,3-dimethyl derivative,
1-(4-phenoxybenzyl)-3,3-dimethyl derivative,
1-(2,3-diphenoxybenzyl)-3,3-dimethyl derivative,
1-(2,4-diphenoxybenzyl)-3,3-dimethyl derivative,
1-(2,5-diphenoxybenzyl)-3,3-dimethyl derivative,
1-(2,6-diphenoxybenzyl)-3,3-dimethyl derivative,
1-(3,4-diphenoxybenzyl)-3,3-dimethyl derivative,
1-(3,5-diphenoxybenzyl)-3,3-dimethyl derivative,
1-(2-methylbenzyl)-3,3-dimethyl derivative,
1-(3-methylbenzyl)-3,3-dimethyl derivative,
1-(4-methylbenzyl)-3,3-dimethyl derivative,
1-(2,3-dimethylbenzyl)-3,3-dimethyl derivative,
1-(2,4-dimethylbenzyl)-3,3-dimethyl derivative,
1-(2,5-dimethylbenzyl)-3,3-dimethyl derivative,
1-(2,6-dimethylbenzyl)-3,3-dimethyl derivative,
1-(3,4-dimethylbenzyl)-3,3-dimethyl derivative,
1-(3,5-dimethylbenzyl)-3,3-dimethyl derivative,
1-(2,3,4-trimethylbenzyl)-3,3-dimethyl derivative,
1-(2,3,5-trimethylbenzyl)-3,3-dimethyl derivative,
1-(2,3,6-trimethylbenzyl)-3,3-dimethyl derivative,
1-(2,4,5-trimethylbenzyl)-3,3-dimethyl derivative,
1-(2,4,6-trimethylbenzyl)-3,3-dimethyl derivative,
1-(3,4,5-trimethylbenzyl)-3,3-dimethyl derivative,
1-(2,3,4,5-tetramethylbenzyl)-3,3-dimethyl derivative,
1-(2,3,4,6-tetramethylbenzyl)-3,3-dimethyl derivative,
1-(2,3,5,6-tetramethylbenzyl)-3,3-dimethyl derivative,
1-(2,3,4,5,6-pentamethylbenzyl)-3,3-dimethyl derivative,
1-(2-ethylbenzyl)-3,3-dimethyl derivative,
1-(3-ethylbenzyl)-3,3-dimethyl derivative,
1-(4-ethylbenzyl)-3,3-dimethyl derivative,
1-(2,3-diethylbenzyl)-3,3-dimethyl derivative,
1-(2,4-diethylbenzyl)-3,3-dimethyl derivative,
1-(2,5-diethylbenzyl)-3,3-dimethyl derivative,
1-(2,6-diethylbenzyl)-3,3-dimethyl derivative,
1-(3,4-diethylbenzyl)-3,3-dimethyl derivative,
1-(3,5-diethylbenzyl)-3,3-dimethyl derivative,
1-(2-t-butylbenzyl)-3,3-dimethyl derivative,
1-(3-t-butylbenzyl)-3,3-dimethyl derivative,
1-(4-t-butylbenzyl)-3,3-dimethyl derivative,
1-(2-fluorobenzyl)-3,3-dimethyl derivative,
1-(3-fluorobenzyl)-3,3-dimethyl derivative,
1-(4-fluorobenzyl)-3,3-dimethyl derivative,
1-(2,3-difluorobenzyl)-3,3-dimethyl derivative,
1-(2,4-difluorobenzyl)-3,3-dimethyl derivative,
1-(2,5-difluorobenzyl)-3,3-dimethyl derivative,
1-(2,6-difluorobenzyl)-3,3-dimethyl derivative,
1-(3,4-difluorobenzyl)-3,3-dimethyl derivative,
1-(3,5-difluorobenzyl)-3,3-dimethyl derivative,
1-(2,3,4-trifluorobenzyl)-3,3-dimethyl derivative,
1-(2,3,5-trifluorobenzyl)-3,3-dimethyl derivative,
1-(2,3,6-trifulorobenzyl)-3,3-dimethyl derivative,
1-(2,4,5-trifluorobenzyl)-3,3-dimethyl derivative,
1-(2,4,6-trifluorobenzyl)-3,3-dimethyl derivative,
1-(3,4,5-trifluorobenzyl)-3,3-dimethyl derivative,
1-(2,3,45-tetrafluorobenzyl)-3,3-dimethyl derivative,
1-(2,3,4,6-tetrafluorobenzyl)-3,3-dimethyl derivative,
1-(2,3,5,6-tetrafluorobenzyl)-3,3-dimethyl derivative,
1-(2,3,4,5,6-pentafluorobenzyl)-3,3-dimethyl derivative,
1-(2-chlorobenzyl)-3,3-dimethyl derivative,
1-(3-chlorobenzyl)-3,3-dimethyl derivative,
1-(4-chlorobenzyl)-3,3-dimethyl derivative,
1-(2,3-dichlorobenzyl)-3,3-dimethyl derivative,
1-(2,4-dichlorobenzyl)-3,3-dimethyl derivative,
1-(2,5-dichlorobenzyl)-3,3-dimethyl derivative,
1-(2,6-dichlorobenzyl)-3,3-dimethyl derivative, 1-(3,4-dichlorobenzyl)-3,3-dimethyl derivative,
1-(3,5-dichlorobenzyl)-3,3-dimethyl derivative,
1-(2,3,4-trichlorobenzyl)-3,3-dimethyl derivative,
1-(2,3,5-trichlorobenzyl)-3,3-dimethyl derivative,
1-(2,3,6-trichlorobenzyl)-3,3-dimethyl derivative,
1-(2,4,5-trichlorobenzyl)-3,3-dimethyl derivative,
1-(2,4,6-trichlorobenzyl)-3,3-dimethyl derivative,
1-(3,4,5-trichlorobenzyl)-3,3-dimethyl derivative,
1-(2-bromobenzyl)-3,3-dimethyl derivative,
1-(3-bromobenzyl)-3,3-dimethyl derivative,
1-(4-bromobenzyl)-3,3-dimethyl derivative,
1-(2,3-dibromobenzyl)-3,3-dimethyl derivative,
1-(2,4-dibromobenzyl)-3,3-dimethyl derivative,
1-(2,5-dibromobenzyl)-3,3-dimethyl derivative,
1-(2,6-dibromobenzyl)-3,3-dimethyl derivative,
1-(3,4-dibromobenzyl)-3,3-dimethyl derivative,
1-(3,5-dibromobenzyl)-3,3-dimethyl derivative,
1-(2-iodobenzyl)-3,3-dimethyl derivative,
1-(3-iodobenzyl)-3,3-dimethyl derivative,
1-(4-iodobenzyl)-3,3-dimethyl derivative,
1-(2-cyanobenzyl)-3,3-dimethyl derivative,
1-(3-cyanobenzyl)-3,3-dimethyl derivative,
1-(4-cyanobenzyl)-3,3-dimethyl derivative,
1-(2,3-dicyanobenzyl)-3,3-dimethyl derivative,
1-(2,4-dicyanobenzyl)-3,3-dimethyl derivative,
1-(2,5-dicyanobenzyl)-3,3-dimethyl derivative,
1-(2,6-dicyanobenzyl)-3,3-dimethyl derivative,
1-(3,4-dicyanobenzyl)-3,3-dimethyl derivative,
1-(3,5-dicyanobenzyl)-3,3-dimethyl derivative,
1-(2-carboxybenzyl)-3,3-dimethyl derivative,
1-(3-carboxybenzyl)-3,3-dimethyl derivative,
1-(4-carboxybenzyl)-3,3-dimethyl derivative,
1-(2-ethoxycarbonylbenzyl)-3,3-dimethyl derivative,
1-(3-ethoxycarbonylbenzyl)-3,3-dimethyl derivative,
1-(4-ethoxycarbonylbenzyl)-3,3-dimethyl derivative,
1-(2-acetylbenzyl)-3,3-dimethyl derivative,
1-(3-acetylbenzyl)-3,3-dimethyl derivative,
1-(4-acetylbenzyl)-3,3-dimethyl derivative,
1-(2-benzoylbenzyl)-3,3-dimethyl derivative,
1-(3-benzoylbenzyl)-3,3-dimethyl derivative,
1-(4-benzoylbenzyl)-3,3-dimethyl derivative,
1-(2-trifluoromethylbenzyl)-3,3-dimethyl derivative,
1-(3-trifluoromethylbenzyl)-3,3-dimethyl derivative,
1-(4-trifluoromethylbenzyl)-3,3-dimethyl derivative,
1-[2,3-bis(trifluoromethyl)benzyl]-3,3-dimethyl derivative,
1-[2,4-bis(trifluoromethyl)benzyl]-3,3-dimethyl derivative,
1-[2,5-bis(trifluoromethyl)benzyl]-3,3-dimethyl derivative,
1-[2,6-bis(trifluoromethyl)benzyl]-3,3-dimethyl derivative,
1-[3,4-bis(trifluoromethyl)benzyl]-3,3-dimethyl derivative,
1-[3,5-bis(trifluoromethyl)benzyl]-3,3-dimethyl derivative,
1-(2-trichloromethylbenzyl)-3,3-dimethyl derivative,
1-(3-trichloromethylbenzyl)-3,3-dimethyl derivative,
1-(4-trichloromethylbenzyl)-3,3-dimethyl derivative,
1-(2-nitrobenzyl)-3,3-dimethyl derivative,
1-(3-nitrobenzyl)-3,3-dimethyl derivative,
1-(4-nitrobenzyl)-3,3-dimethyl derivative,
1-(2,3-dinitrobenzyl)-3,3-dimethyl derivative,
1-(2,4-dinitrobenzyl)-3,3-dimethyl derivative,
1-(2,5-dinitrobenzyl)-3,3-dimethyl derivative,
1-(2,6-dinitrobenzyl)-3,3-dimethyl derivative,
1-(3,4-dinitrobenzyl)-3,3-dimethyl derivative,
1-(3,5-dinitrobenzyl)-3,3-dimethyl derivative,
1-(2-methoxy-5-nitrobenzyl)-3,3-dimethyl derivative,
1-(2-hydroxy-5-nitrobenzyl)-3,3-dimethyl derivative,
1-(3,5-dibromo-2-hydroxybenzyl)-3,3-dimethyl derivative,
1-(3,5-dibromo-4-hydroxybenzyl)-3,3-dimethyl derivative,
1-(2-phenylethyl)-3,3-dimethyl derivative,
1-[2-(2-methoxyphenyl)ethyl]-3,3-dimethyl derivative,
1-[2-(3-methoxyphenyl)ethyl]-3,3-dimethyl derivative,
1-[2-(4-methoxyphenyl)ethyl]-3,3-dimethyl derivative,
1-[2-(2,3-dimethoxyphenyl)ethyl]-3,3-dimethyl derivative,
1-[2-(2,4-dimethoxyphenyl)ethyl]-3,3-dimethyl derivative,
1-[2-(2,5-dimethoxyphenyl)ethyl]-3,3-dimethyl derivative,
1-[2-(2,6-dimethoxyphenyl)ethyl]-3,3-dimethyl derivative,
1-[2-(3,4-dimethoxyphenyl)ethyl]-3,3-dimethyl derivative,
1-[2-(3,5-dimethoxyphenyl)ethyl]-3,3-dimethyl derivative,
1-[2-(2-methylphenyl)ethyl]-3,3-dimethyl derivative
1-[2-(3-methylphenyl)ethyl]-3,3-dimethyl derivative
1-[2-(4-methylphenyl)ethyl]-3,3-dimethyl derivative
1-[2-(2,3-dimethylphenyl)ethyl]-3,3-dimethyl derivative,
1-[2-(2,4-dimethylphenyl)ethyl]-3,3-dimethyl derivative,
1-[2-(2,5-dimethylphenyl)ethyl]-3,3-dimethyl derivative,
1-[2-(2,6-dimethylphenyl)ethyl]-3,3-dimethyl derivative,
1-[2-(3,4-dimethylphenyl)ethyl]-3,3-dimethyl derivative,
1-[2-(3,5-dimethylphenyl)ethyl]-3,3-dimethyl derivative,
1-[2-(2-fluorophenyl)ethyl]-3,3-dimethyl derivative,
1-[2-(3-fluorophenyl)ethyl]-3,3-dimethyl derivative,
1-[2-(4-fluorophenyl)ethyl]-3,3-dimethyl derivative,
1-[2-(2,3-difluorophenyl)ethyl]-3,3-dimethyl derivative,
1-[2-(2,4-difluorophenyl)ethyl]-3,3-dimethyl derivative,
1-[2-(2,5-difluorophenyl)ethyl]-3,3-dimethyl derivative,
1-[2-(2,6-difluorophenyl)ethyl]-3,3-dimethyl derivative,
1-[2-(3,4-difluorophenyl)ethyl]-3,3-dimethyl derivative,
1-[2-(3,5-difluorophenyl)ethyl]-3,3-dimethyl derivative,
1-[2-(2-chlorophenyl)ethyl]-3,3-dimethyl derivative,
1-[2-(3-chlorophenyl)ethyl]-3,3-dimethyl derivative,
1-[2-(4-chlorophenyl)ethyl]-3,3-dimethyl derivative,
1-[2-(2-bromophenyl)ethyl]-3,3-dimethyl derivative,
1-[2-(3-bromophenyl)ethyl]-3,3-dimethyl derivative,
1-[2-(4-bromophenyl)ethyl]-3,3-dimethyl derivative,
1-[2-(2-trifluoromethylphenyl)ethyl]-3,3-dimethyl derivative,
1-[2-(3-trifluoromethylphenyl)ethyl]-3,3-dimethyl derivative,
1-[2-(4-trifluoromethylphenyl)ethyl]-3,3-dimethyl derivative,
1-[2-(2-nitrophenyl)ethyl]-3,3-dimethyl derivative,
1-[2-(3-nitrophenyl)ethyl]-3,3-dimethyl derivative,
1-[2-(4-nitrophenyl)ethyl]-3,3-dimethyl derivative,
1-(3-phenylpropyl)-3,3-dimethyl derivative,
1-[3-(2-methoxyphenyl)propyl]-3,3-dimethyl derivative,
1-[3-(3-methoxyphenyl)propyl]-3,3-dimethyl derivative,
1-[3-(4-methoxyphenyl)propyl]-3,3-dimethyl derivative, 1-[3-(2-methylphenyl)propyl]-3,3-dimethyl derivative,
1-[3-(3-methylphenyl)propyl]-3,3-dimethyl derivative,
1-[3-(4-methylphenyl)propyl]-3,3-dimethyl derivative,
1-[3-(2-fluorophenyl)propyl]-3,3-dimethyl derivative,
1-[3-(3-fluorophenyl)propyl]-3,3-dimethyl derivative,
1-[3-(4-fluorophenyl)propyl]-3,3-dimethyl derivative,
1-[3-(2,3-difluorophenyl)propyl]-3,3-dimethyl derivative,
1-[3-(2,4-difluorophenyl)propyl]-3,3-dimethyl derivative,
1-[3-(2,5-difluorophenyl)propyl]-3,3-dimethyl derivative,
1-[3-(2,6-difluorophenyl)propyl]-3,3-dimethyl derivative,
1-[3-(3,4-difluorophenyl)propyl]-3,3-dimethyl derivative,
1-[3-(3,5-difluorophenyl)propyl]-3,3-dimethyl derivative,
1-[3-(2-trifluoromethylphenyl)propyl]-3,3-dimethyl derivative,
1-[3-(3-trifluoromethylphenyl)propyl]-3,3-dimethyl derivative,
1-[3-(4-trifluoromethylphenyl)propyl]-3,3-dimethyl derivative,
1-[3-(2-nitrophenyl)propyl]-3,3-dimethyl derivative,
1-[3-(3-nitrophenyl)propyl]-3,3-dimethyl derivative,
1-[3-(4-nitrophenyl)propyl]-3,3-dimethyl derivative,
1-[3-(4-phenylbutyl)-3,3-dimethyl derivative,
1-[4-(2-methoxyphenyl)butyl]-3,3-dimethyl derivative,
1-[4-(3-methoxyphenyl)butyl]-3,3-dimethyl derivative,
1-[4-(4-methoxyphenyl)butyl]-3,3-dimethyl derivative,
1-[4-(4-fluorophenyl)butyl]-3,3-dimethyl derivative,
1-[4-(2-nitrophenyl)butyl]-3,3-dimethyl derivative,
1-[4-(3-nitrophenyl)butyl]-3,3-dimethyl derivative,
1-[4-(4-nitrophenyl)butyl]-3,3-dimethyl derivative,
1-(5-phenylheptyl)-3,3-dimethyl derivative,
1-[5-(2-methoxyphenyl)heptyl]-3,3-dimethyl derivative,
1-[5-(3-methoxyphenyl)heptyl]-3,3-dimethyl derivative,
1-[5-(4-methoxyphenyl)heptyl]-3,3-dimethyl derivative,
1-[5-(4-fluorophenyl)heptyl]-3,3-dimethyl derivative,
1-[5-(2-nitrophenyl)heptyl]-3,3-dimethyl derivative,
1-[5-(3-nitrophenyl)heptyl]-3,3-dimethyl derivative,
1-[5-(4-nitrophenyl)heptyl]-3,3-dimethyl derivative,
1-[(1-naphthyl)methyl]-3,3-dimethyl derivative,
1-[(2-methoxy-1-naphthyl)methyl]-3,3-dimethy derivative,
1-[(3-methoxy-1-naphthyl)methyl]-3,3-dimethyl derivative,
1-[(4-methoxy-1-naphthyl)methyl]-3,3-dimethyl derivative,
1-[(5-methoxy-1-naphthyl)methyl]-3,3-dimethyl derivative,
1-[(6-ethoxy-1-naphthyl)methyl]-3,3-dimethyl derivative,
1-[(7-ethoxy-1-naphthyl)methyl]-3,3-dimethyl derivative,
1-[(8-ethoxy-1-naphthyl)methyl]-3,3-dimethyl derivative,
1-[(2-methyl-1-naphthyl)methyl]-3,3-dimethyl derivative,
1-[(3-methyl-1-naphthyl)methyl]-3,3-dimethyl derivative,
1-[(4-methyl-1-naphthyl)methyl]-3,3-dimethyl derivative,
1-[(5-ethyl-1-naphthyl)methyl]-3,3-dimethyl derivative,
1-[(6-ethyl-1-naphthyl)methyl]-3,3-dimethyl derivative,
1-[(7-butyl-1-naphthyl)methyl]-3,3-dimethyl derivative,
1-[(8-butyl-1-naphthyl)methyl]-3,3-dimethyl derivative,
1-[(2-nitro-1-naphthyl)methyl]-3,3-dimethyl derivative,
1-[(3-nitro-1-naphthyl)methyl]-3,3-dimethyl derivative,
1-[(4-nitro-1-naphthyl)methyl]-3,3-dimethyl derivative,
1-[(5-nitro-1-naphthyl)methyl]-3,3-dimethyl derivative,
1-[(6-nitro-1-naphthyl)methyl]-3,3-dimethyl derivative,
1-[(7-nitro-1-naphthyl)methyl]-3,3-dimethyl derivative,
1-[(8-nitro-1-naphthyl)methyl]-3,3-dimethyl derivative,
1-[(2-(1-naphthyl)ethyl]-3,3-dimethyl derivative,
1-[(2-(2-ethoxy-1-naphthyl)ethyl]-3,3-dimethyl derivative,
1-[(2-(3-ethoxy-1-naphthyl)ethyl]-3,3-dimethyl derivative,
1-[(2-(4-ethoxy-1-naphthyl)ethyl]-3,3-dimethyl derivative,
1-[(2-(5-methoxy-1-naphthyl)ethyl]-3,3-dimethyl derivative,
1-[(2-(6-methoxy-1-naphthyl)ethyl]-3,3-dimethyl derivative,
1-[(2-(7-methoxy-1-naphthyl)ethyl]-3,3-dimethyl derivative,
1-[(2-(8-methoxy-1-naphthyl)ethyl]-3,3-dimethyl derivative,
1-[(2-(2-ethyl-1-naphthyl)ethyl]-3,3-dimethyl derivative,
1-[(2-(3-ethyl-1-naphthyl)ethyl]-3,3-dimethyl derivative,
1-[(2-(4-butyl-1-naphthyl)ethyl]-3,3-dimethyl derivative,
1-[(2-(5-butyl-1-naphthyl)ethyl]-3,3-dimethyl derivative,
1-[(2-(6-methyl-1-naphthyl)ethyl]-3,3-dimethyl derivative,
1-[2-(7-methyl-1-naphthyl)ethyl]-3,3-dimethyl derivative,
1-[2-(8-methyl-1-naphthyl)ethyl]-3,3-dimethyl derivative,
1-[2-(2-nitro-1-naphthyl)ethyl]-3,3-dimethyl derivative,
1-[2-(3-nitro-1-naphthyl)ethyl]-3,3-dimethyl derivative,
1-[2-(4-nitro-1-naphthyl)ethyl]-3,3-dimethyl derivative,
1-[2-(5-nitro-1-naphthyl)ethyl]-3,3-dimethyl derivative,
1-[2-(6-nitro-1-naphthyl)ethyl]-3,3-dimethyl derivative,
1-[2-(7-nitro-1-naphthyl)ethyl]-3,3-dimethyl derivative,
1-[2-(8-nitro-1-naphthyl)ethyl]-3,3-dimethyl derivative,
1-[3-(1-naphthyl)propyl]-3,3-dimethyl derivative,
1-[3-(2-methoxy-1-naphthyl)propyl]-3,3-dimethyl derivative,
1-[3-(3-methyl-1-naphthyl)propyl]-3,3-dimethyl derivative,
1-[3-(4-fluoro-1-naphthyl)propyl]-3,3-dimethyl derivative,
1-[3-(5-nitro-1-naphthyl)propyl]-3,3-dimethyl derivative,
1-[4-(1-naphthyl)butyl]-3,3-dimethyl derivative,
1-[4-(6-methoxy-1-naphthyl)butyl]-3,3-dimethyl derivative,
1-[4-(7-methyl-1-naphthyl)butyl]-3,3-dimethyl derivative,
1-[4-(8-chloro-1-naphthyl)butyl]-3,3-dimethyl derivative,
1-[4-(2-nitro-1-naphthyl)butyl]-3,3-dimethyl derivative,
1-[5-(1-naphthyl)heptyl]-3,3-dimethyl derivative,
1-[5-(3-ethoxy-1-naphthyl)heptyl]-3,3-dimethyl derivative,
1-[5-(4-ethyl-1-naphthyl)heptyl]-3,3-dimethyl derivative,
1-[5-(5-bromo-1-naphthyl)heptyl]-3,3-dimethyl derivative, 1-[5-(6-cyano-1-naphthyl)heptyl]-3,3-dimethyl derivative,
1-[(2-naphthyl)methyl -3,3-dimethyl]derivative,
1-[(1-methoxy-2-naphthyl)methyl]-3,3-dimethyl derivative,
1-[(3-methoxy-2-naphthyl)methyl]-3,3-dimethyl derivative,
1-[(4-methoxy-2-naphthyl)methyl]-3,3-dimethyl derivative,
1-[(5-methoxy-2-naphthyl)methyl]-3,3-dimethyl derivative,
1-[(6-ethoxy-2-naphthyl)methyl]-3,3-dimethyl derivative,
1-[(7-ethoxy-2-naphthyl)methyl]-3,3-dimethyl derivative,
1-[(8-ethoxy-2-naphthyl)methyl]-3,3-dimethyl derivative,
1-[(1-methyl-2-naphthyl)methyl]-3,3-dimethyl derivative,
1-[(3-methyl-2-naphthyl)methyl]-3,3-dimethyl derivative,
1-[(4-propyl-2-naphthyl)methyl]-3,3-dimethyl derivative,
1-[(5-propyl-2-naphthyl)methyl]-3,3-dimethyl derivative,
1-[(6-t-butyl-2-naphthyl)methyl]-3,3-dimethyl derivative,
1-[(7-methyl-2-naphthyl)methyl]-3,3-dimethyl derivative,
1-[(8-methyl-2-naphthyl)methyl]-3,3-dimethyl derivative,
1-[(1-nitro-2-naphthyl)methyl]-3,3-dimethyl derivative,
1-[(3-nitro-2-naphthyl)methyl]-3,3-dimethyl derivative,
1-[(4-nitro-2-naphthyl)methyl]-3,3-dimethyl derivative,
1-[(5-nitro-2-naphthyl)methyl]-3,3-dimethyl derivative,
1-[(6-nitro-2-naphthyl)methyl]-3,3-dimethyl derivative,
1-[(7-nitro-2-naphthyl)methyl]-3,3-dimethyl derivative,
1-[(8-nitro-2-naphthyl)methyl]-3,3-dimethyl derivative,
1-[2-(2-naphthyl)ethyl]-3,3-dimethyl derivative,
1-[2-(1-ethoxy-2-naphthyl)ethyl]-3,3-dimethyl derivative,
1-[2-(3-ethoxy-2-naphthyl)ethyl]-3,3-dimethyl derivative,
1-[2-(4-t-butoxy-2-naphthyl)ethyl]-3,3-dimethyl derivative,
1-[2-(5-t-butoxy-2-naphthyl)ethyl]-3,3-dimethyl derivative,
1-[2-(6-methoxy-2-naphthyl)ethyl]-3,3-dimethyl derivative,
1-[2-(7-methoxy-2-naphthyl)ethyl]-3,3-dimethyl derivative,
1-[2-(8-methoxy-2-naphthyl)ethyl]-3,3-dimethyl derivative,
1-[2-(1-ethyl-2-naphthyl)ethyl]-3,3-dimethyl derivative,
1-[2-(3-ethyl-2-naphthyl)ethyl]-3,3-dimethyl derivative,
1-[2-(4-butyl-2-naphthyl)ethyl]-3,3-dimethyl derivative,
1-[2-(5-butyl-2-naphthyl)ethyl]-3,3-dimethyl derivative,
1-[2-(6-methyl-2-naphthyl)ethyl]-3,3-dimethyl derivative,
1-[2-(7-methyl-2-naphthyl)ethyl]-3,3-dimethyl derivative,
1-[2-(8-methyl-2-naphthyl)ethyl]-3,3-dimethyl derivative,
1-[2-(1-cyano-2-naphthyl)ethyl]-3,3-dimethyl derivative,
1-[2-(3-cyano-2-naphthyl)ethyl]-3,3-dimethyl derivative,
1-[2-(4-nitro-2-naphthyl)ethyl]-3,3-dimethyl derivative,
1-[2-(5-nitro-2-naphthyl)ethyl]-3,3-dimethyl derivative,
1-[2-(6-nitro-2-naphthyl)ethyl]-3,3-dimethyl derivative,
1-[2-(7-nitro-2-naphthyl)ethyl]-3,3-dimethyl derivative,
1-[2-(8-nitro-2-naphthyl)ethyl]-3,3-dimethyl derivative,
1-[3-(2-naphthyl)propyl -3,3-dimethyl]derivative,
1-[3-(1-methoxy-2-naphthyl)propyl]-3,3-dimethyl derivative,
1-[3-(3-methyl-2-naphthyl)propyl]-3,3-dimethyl derivative,
1-[3-(4-fluoro-2-naphthyl)propyl]-3,3-dimethyl derivative,
1-[3-(5-nitro-2-naphthyl)propyl]-3,3-dimethyl derivative,
1-[4-(2-naphthyl)butyl -3,3-dimethyl]derivative,
1-[4-(6-ethoxy-2-naphthyl)butyl]-3,3-dimethyl derivative,
1-[4-(7-ethyl-2-naphthyl)butyl]-3,3-dimethyl derivative,
1-[4-(8-bromo-2-naphthyl)butyl]-3,3-dimethyl derivative,
1-[4-(1-nitro-2-naphthyl)butyl]-3,3-dimethyl derivative,
1-[5-(2-naphthyl)heptyl]-3,3-dimetyl derivative,
1-[5-(3-t-butoxy-2-naphthyl)heptyl]-3,3-dimethyl derivative,
1-[5-(4-propyl-2-naphthyl)naphthyl)heptyl]-3,3-dimethyl derivative,
1-[5-(5-fluoro-2-naphthyl)heptyl]-3,3-dimethyl derivative, and
1-[5-(6-carboxy-2-naphthyl)heptyl]-3,3-dimethyl derivative.

The novel spiro-oxazine compound of the present invention represented by the formula (A) is a photochromic compound characterized in that it is excellent in the fatigue resistance to repeated coloration and decolorization by light and the absorption wavelength for coloration can be freely changed in a broad range by changing kinds of the substituents and matrix resin.

The spiro-oxazine compound of the present invention represented by the formula (A) is prepared, for example, according to the method wherein a precursor of the spiro-oxazine compound of the formula (A), which has a substituent of the formula: $-(CH_2)_nR$ (R is the same as defined above) in the nitrogen atom of the indoline nucleus, is reacted with an α-nitroso-β-naphthol of the following formula:

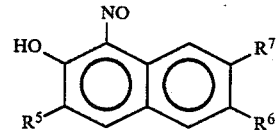

wherein $R^5$, $R^6$ and $R^7$ are the same as defined above.

More specifically, the spiro-oxazine compound of the formula (A) is prepared by the method which comprises the steps of:

(i) reacting a compound represented by the following formula (D) with an aralkyl halide $R(CH_2)_nX$ or a sulfonate derivative $R(CH_2)_n-O-SO_2R'$,

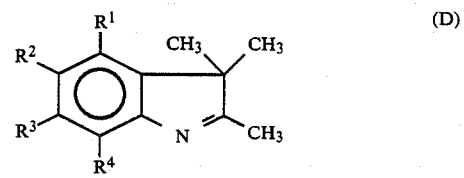

wherein $R^1$, $R^2$, $R^3$, $R^4$, R, and n are the same as defined above; R' represents an alkyl group having 1 to 8 carbon atoms, a halogenated alkyl group having 1 to 8 carbon atoms, a halogenated phenyl group, a nitrosubstituted alkyl group having 1 to 8 carbon atoms, a nitro-substituted phenyl group or a phenyl group having an alkyl substituent having 1 to 8 carbon atoms; and X represents a halogen atom such as fluorine, chlorine, bromine or iodine;

(ii) reacting the reaction mixture, formed by the reaction in the step (i), with a basic substance, and (iii) reacting the reaction mixture formed by the reaction in the step (ii), with an α-nitroso-β-naphthol of the formula:

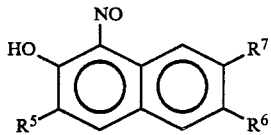

wherein $R^5$, $R^6$ and $R^7$ are the same as defined above.

In the method for the preparation of the spirooxazine compound of the formula (A), the trimethylindolenine derivative represented by the formula (D) is used as the starting substance, and the spiro-oxazine compound of the formula (A) is yielded through the above-mentioned three sequential reactions. Each of the intermediate products obtained at these sequential reactions, that is, the product of the reaction of the first step and the product of the reaction of the second step, are difficult to isolate, and therefore, the chemical structures of these intermediate products are indefinite. However, from the chemical structures of the reactants used for the sequential reactions and the finally obtained spirooxazine compound, it is presumed that the product of the reaction of the first step is represented by the following formula (C):

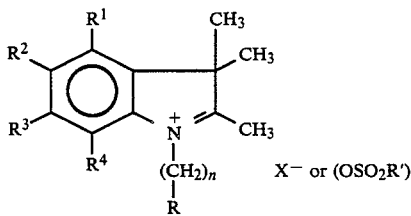

and the product of the reaction of the second step is represented by the following formula (B):

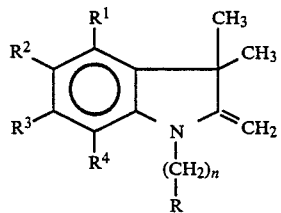

wherein $R^1$, $R^2$, $R^3$, $R^4$, R and n are the same as defined above.

In carrying out the above-mentioned sequential reactions, the order of addition of the reactants to be used for the reactions, that is, the reactant of the first step reaction (aralkyl halide or sulfonate derivative), the reactant of the second step reaction (basic substance) and the reactant of the third step reaction (α-nitroso-β-naphthol), is not particularly critical. Generally, the reactants are added to the reaction system according to any of the following five-procedures.

(1) The reactant of the first step reaction, the reactant of the second step reaction and the reactant of the third step reaction are sequentially added in this order to the compound of formula (D).

(2) The reactant of the first step reaction is first added to the compound of formula (D), and both the reactant of the second step reaction and the reactant of the third step reaction are then added.

(3) Both the reactant of the second step reaction and the reactant of the third step reactant are first added to the compound of formula (D) and the reactant of the first step reaction is then added.

(4) The reactant of the first step reaction, the reactant of the third step reaction and the reactant of the second step reaction are sequentially added in this order to the compound of the formula (D).

(5) The reactant of the first step reaction, the reactant of the second step reaction and the reactant of the third step reaction are simultaneously added to the compound of formula (D).

The trimethylindolenine derivative of formula (D) used in the present invention may be synthesized, for example, by cyclization of methylisopropyl ketone with a substituted phenylhydrazine [Helv. Chim. Acta., 23, 2471 (1940)].

The reactivity of the aralkyl halide $R(CH_2)_nX$ used for the reaction of the first step is greatly influenced by the halogen atom X. Namely, the reactivity is generally higher in the order of iodine > bromine > chlorine >> fluorine. The reactivity is also influenced by the aralkyl group. The electronic effect is mainly influential, and the reactivrty is lower when the reactant has an electron-withdrawing substituent, while the reactivity is higher when the reactant has an electron-donative substituent.

The sulfonate derivative $R\text{-}(CH_2)_n\text{—O—}SO_2\text{-}R'$ used for the reaction of the first step may be synthesized according to known methods, for example, a method in which an aralkyl alcohol is reacted with a sulfonate halide (Organic Synthesis, Collective Vol. 1, 145).

As the R' in the sulfonate group, there can be mentioned alkyl groups having 1 to 8 carbon atoms, halogenated alkyl groups having 1 to 8 carbon atoms, halogenated phenyl groups, nitro-substituted alkyl groups having 1 to 8 carbon atoms, nitro-substituted phenyl groups and alkyl-substituted phenyl groups. From the viewpoint of the reactivity, a halogenated alkyl group, a p-substituted phenyl group and an alkyl group having 1 to 4 carbon atoms are preferred. Especially preferred examples are a trifluoromethyl group, a 2,2,2-trifluoroethyl group, a p-methylphenyl group, a p-bromophenyl group, a p-nitrophenyl group and a butyl group. The sulfonate derivatives include, for example, benzyl tosylate (tosylate is an abbreviation for p-toluene-sulfonate), 2-phenylethyl tosylate, benzyl brosylate (brosylate is an abbreviation for p-bromobenzene-sulfonate), and (1-naphthyl)methyltrifluoromethane-sulfonate.

Any organic and inorganic basic substance can be used as the basic substance for the reaction of the second step, but amines such as pyridine, piperidine and triethylamine are preferable.

The α-nitroso-β-naphthol derivative used for the reaction of the third step may be synthesized, for example, by nitrosation of a substituted naphthol.

Any solvent other than water may be used in the method for the preparation of the spiro-oxazine compounds, but in view of easiness of removal of the solvent after the reaction and easiness of control of the reaction temperature, it is preferable that an organic solvent having a boiling point of 30° to 180° C. be used.

For example, the solvents include hydrocarbons such as benzene, toluene, xylene, and hexane; chlorides such as chloroform and methylene chloride; sulfides such as carbon disulfide and dimethyl sulfoxide; polar aprotic solvents such as acetone, methyl ethyl ketone, ethyl acetate and acetonitrile; ethers such as tetrahydrofuran and dioxane; and polar protic solvents such as methanol, ethanol, methyl cellosolve and ethyl cellosolve. It is preferable that the solvent be used after dehydration.

The conditions for the reaction of the trimethylindolenine derivative represented by the general formula (D) with the aralkyl halide or sulfonate derivative are experimentally determined according to the kinds of the trimethylindolenine derivative, the aralkyl halide or sulfonate derivative and the reaction solvent. It is especially preferable that the reaction be carried out for 0.1 to 8 hours at the reflux temperature of the solvent used or a temperature close thereto. The reaction of the trimethylindolenine derivative with the aralkyl halide or sulfonate derivative may be advanced by heating after mixing of both the reactants. However, in order to prevent reduction of the yield of the intermediate product by oxidation or decomposition, it is preferable to adopt a method in which the respective reactants are independently dissolved in the reaction solvent before mixing, the respective atmospheres of the resultant solutions are flushed with an inert gas, the solutions are mixed together, and heating is then performed. As the inert gas, nitrogen, helium or argon is used. It is preferable that the aralkyl halide or sulfonate derivative be used in an amount of 0.5 to 8 moles, more preferably 0.8 to 2 moles, per mole of the trimethylindolenine derivative.

It is preferable that the reaction of the product of the reaction of the first step with the basic substance be carried out at a temperature of 0° to 120° C., more preferably 30° to 90° C. The basic substance is used in an amount of 0.5 to 20 moles, preferably 0.8 to 2 moles, per mole of the trimethylindolenine derivative.

After the reaction of the product of the reaction of the first step with the basic substance, the final reaction of the formed substance with α-nitroso-β-naphthol is carried out. It is preferable that this reaction be carried out at 10° to 160° C. for 1 minute to 8 hours. It is more preferable that the reaction be carried out for 0.5 to 4 hours at the reflux temperature of the solvent used or a temperature close thereto. The α-nitroso-β-naphthol is used in an amount of 0.2 to 2 moles, preferably 0.5 to 1.5 moles, per mole of the trrmethylindolenine derrvative.

In the case where the reaction temperature or time is lower or shorter than the lower limit or shorter limit, the reaction is not sufficiently advanced and the yield of the spiro-oxazine compound as the final product is low. In the case where the reaction temperature or time is higher or longer than the higher limit or longer limit, the reaction product and/or the starting compounds are thermally decomposed and the yield of the final product is low. If the molar ratio of the reactants is outside the above-mentioned range, the yield of the final product is reduced and isolation of the final product becomes difficult.

Separation and purification of the final product, that is, the spiro-oxazine compounds represented by the general formula (A), can be accomplished by a recrystallization method using various solvents, a column chromatography separation method using various supporting carriers and organic solvents and an active carbon treatment method using various solvents. Moreover, a composite treatment employing these methods in combination can be adopted.

Any solvent capable of dissolving the spiro-oxazine derivative therein can be used for the recrystallization. The solvents may be used singly or in the form of the mixture of two or more. The solvents include, for example, hydrocarbons such as benzene, toluene, xylene and hexane; chlorides such as chloroform and methylene chloride; sulfides such as carbon disulfide and dimethylsulfoxide; polar aprotic solvents such as acetone, methyl ethyl ketone, ethyl acetate and acetonitrile; ethers such as tetrahydrofuran and dioxane; polar protic solvents such as methyl alcohol, ethyl alcohol, methyl cellosolve and ethylene glycol; and mixtures thereof As specific examples of the supporting carrier used in the column separation method, there can be mentioned silica gel, alumina, cellulose, calcium hydroxide and calcium oxide.

Any solvent capable of dissolving the spiro-oxazine compound but incapable of dissolving the supporting carrier may be used as the developing solvent. The developing solvent includes, for example, hydrocarbons such as benzene, toluene, xylene and hexane; chlorides such as chloroform and methylene chloride; polar aprotic solvents such as acetone, methyl ethyl ketone and ethyl acetate; ethers such as tetrahydrofuran and dioxane, and polar protic solvents such as methanol and ethanol These solvents may be used singly or in the form of a mixture of two or more.

The combination of the supporting carrier and the developing solvent is experimentally determined according to the solubility of the non-separated substance and the effluent speed.

Any solvent capable of dissolving the spiro-oxazine compound therein may be used as the solvent for the active carbon treatment. Either a single solvent or a mixed solvent may be used. The solvents used include, for example, hydrocarbons such as benzene, xylene and hexane; chlorides such as chloroform and methylene chloride; sulfides such as carbon disulfide and dimethyl sulfoxide; polar aprotic solvents such as acetone, methyl ethyl ketone, ethyl acetate and acetonitrile; ethers such as tetrahydrofuran and dioxane; polar protic solvents such as methyl alcohol, ethyl alcohol, methyl cellosolve and ethylene glycol; and mixtures thereof.

The spiro-oxazine compound of the present invention may be formed into a shaped article in combination with an optically transparent material. As one preferred means for combining the spiro-oxazine compound with an optically transparent material, there can be mentioned a method in which a coating of the spiro-oxazine compound and an optically transparent resin is formed on a shaped article which may be made of various organic or inorganic materials. This coating can be formed by dissolving the optically transparent resin in an appropriate solvent, dissolving the spiro-oxazine compound in the resulting solution and coating the solution on a shaped article (for example, a lens, plate, sheet, film or fiber).

The material to be coated with the spiro-oxazine compound includes, for example, organic thermoplastic and thermosetting resins such as a homopolymer or copolymer of methyl methacrylate or other methacrylates, an acrylate homopolymer or copolymer, a styrene homopolymer or copolymer, a polyester resin, a polyamide resin, an epoxy resin, a melamine resin, a polycarbonate resin, polyvinyl acetate, polyvinyl alcohol, polyvinyl butyral, a diethylene glycol bisallylcarbonate polymer (CR-39), natural rubber, synthetic rubber, a homopolymer or copolymer of a bisphenol A (or halogenated bisphenol A) dimethacrylate (or diacrylate) or its urethane-modified homopolymer or copolymer, polyurethane and cellulose; and inorganic materials such as glass, quartz, potassium bromide, metal or ceramics. These coated materials may be either optically transparent or opaque.

The optically transparent resins used for the formation of coatings together with the spiro-oxazine compound include, for example, various organic thermoplastic and thermosetting resins such as polyvinyl acetate, polyvinyl chloride, polyvinyl butyral, polymethyl methacrylate, acetyl cellulose, cellulose acetate butyrate, cellulose acetate propionate, cellulose acetate phthalate, polyvinyl pyrrolidone, polystyrene, hydroxyethyl cellulose, hydroxypropyl cellulose, an epoxy resin, a phenolic resin, a polysiloxane resin and a urethane resin. Among these resins, a polyorganosiloxane is especially preferable.

As specific examples of the solvent used for the preparation of a coating solution, there can be mentioned unsaturated hydrocarbons such as benzene and toluene; polar aprotic solvents such as acetone, methyl ethyl ketone, acetonitrile and dimethylformamide; polar protic solvents such as ethanol and n-butanol; chlorides such as methylene chloride and chloroform; and sulfides such as dimethylsulfoxide.

Another means for combining the spiro-oxazine compound of the present invention with the optically transparent material to form a shaped article comprises including the spiro-oxazine compound substantially uniformly within the optically transparent material. For example, an optically transparent resin as listed above is used as the optically transparent material and dissolved in an appropriate solvent, the spiro-oxazine compound is dissolved in the solution, and then the solution is cast to form a film or sheet.

Furthermore, when the spiro-oxazine compound is added to a polymerizable monomer such as methyl methacrylate, styrene, an epoxy compound or a melamine compound and the monomer is polymerized by using an appropriate polymerization initiator, the spiro-oxazine compound can be contained substantially uniformly in the formed resin. An azo compound such as azobisisobutyronitrile is preferable as the polymerization initiator.

Moreover, the spiro-oxazine compound may be incorporated into a transparent substrate of polycarbonate, polymethyl methacrylate or diethylene glycol bisallylcarbonate polymer (CR-39) by utilizing a dyeing technique. More specifically, a transparent substrate is immersed in a solution or dispersion of the spiro-oxazine derivative in an appropriate solvent, and heating is effected with stirring, whereby the spiro-oxazine derivative is diffused in the transparent substrate.

Still further, the spiro-oxazine compound can be applied to the surface of the shaped article by vacuum evaporation deposition or the like.

The amount of the spiro-oxazine compound of the present invention combined with the optically transparent material or resin should be determined according to the intended object and application method, but in view of the sensitivity to the sense of sight, it is preferable that the spiro-oxazine compound be used in an amount of 0.01 to 20% by weight based on the weight of the shaped article or the coating.

The shaped article made of the optically transparent material and the spiro-oxazine compound can be used as an optical element capable of changing the color by exposure to light or irradiation. As preferred examples of the optical element, there can be mentioned a sunglass lens, skiing goggles, a protecting glass lens, a curtain, a garment, and a toy.

The present invention will now be described in detail with reference to the following examples, which, however, by no means limit the scope of the invention.

EXAMPLE 1

(1) Synthesis of 1-benzyl-3,3-dimethylspiro [indoline-2,3'-[3H]-naphtho[2,1-b](1,4)-oxazine]

15.9 g of 2,3,3-trimethylindolenine was dissolved in 60 ml of absolute ethanol. 34.4 g of benzyl bromide was dissolved in 20 ml of absolute ethanol. Nitrogen gas was bubbled into each solution for 10 minutes. The two solutions were mixed together and refluxed in a nitrogen current for 1 hour. The temperature of the reaction mixture was lowered to 50° C. 10.0 g of triethylamine and 12.0 g of α-nitroso-β-naphthol were added to the reaction mixture and then the mixture was refluxed for 2 hours. When the reaction mixture was cooled after the reaction, a crystal was precipitated. A small amount of ethanol was added and filtration was carried out. The thus obtained crude crystal was dissolved in benzene and the solution was heated at 60° to 70° C. 50 g of active carbon was added to the solution and the mixture was sufficiently stirred. The mixture was filtered and then the filtrate was concentrated. The thus-obtained white solid was recrystallized from ethanol to obtain a white crystal of 1-benzyl-3,3-dimethylspiro[indoline-2,3'-[3H]-naphtho [2,1-b](1,4)-oxazine].

(2) Results of analysis

Melting point: 193°–194° C.
Elementary analysis:

| | Found value (%) | Calculated value (%) |
|---|---|---|
| C | 83.3 | 83.2 |
| H | 5.8 | 5.9 |
| N | 6.8 | 6.9 |

Infrared absorption:
1627 cm$^{-1}$ (C=N), 1250 cm$^{-1}$ (=C—O), 955 cm$^{-1}$ (O—C—N).
Nuclear magnetic resonance
1.4 ppm (6H), 4.4 ppm (2H), 6.3–8.6 ppm (16H).

(3) Application

The compound was dissolved in methyl methacrylate at a concentration of 0.5% by weight. Cast polymerization was carried out by using azobisisobutyronitrile as the polymerization initiator to obtain a plate of polymethyl methacrylate containing the compound of this example incorporated therein. The plate showed a bluish purple color under irradiation with ultraviolet rays.

When the light was removed and the plate was allowed to stand in the dark, the original colorless state was immediately restored. When the plate was exposed to rays from a fade-ometer for 20 hours and the light resistance was examined, it was found that the plate retained the same photochromic characteristics as observed before exposure to the fade-ometer. Thus, the plate was excellent in fatigue resistance.

EXAMPLE 2

(1) Synthesis of 1-(4-methoxybenzyl)-3,3-dimethylspiro[indoline-2,3'-[3H]-naphtho[2,1-b](1,4)-oxazine]

8.0 g of 2,3,3-trimethylindolenine was dissolved in 60 ml of toluene. 18.0 g of 4-methoxybenzyl bromide was dissolved in 20 ml of toluene. Nitrogen gas was bubbled into each solution for 10 minutes. The two solutions were mixed together and refluxed in a nitrogen current for 1 hour. Then, the temperature of the reaction mixture was lowered to 50° C. 5.0 g of piperidine and 6.0 g of α-nitroso-β-naphthol were added to the reaction mixture and then the mixture was refluxed for 2 hours. When the reaction mixture was cooled after the reactron, a crystal was precipitated. Purification was carried out in the same manner as described in Example 1 to obtain a white crystal of 1-(4-methoxybenzyl)-3,3-dimethylspiro[indoline-2,3'-[3H]-naphtho[2,1-b](1,4)-oxazine].

(2) Results of analysis

Melting point: 157°–158° C.
Elementary analysis:

|   | Found value (%) | Calculated values (%) |
|---|---|---|
| C | 80.4 | 80.2 |
| H | 5.8 | 6.0 |
| N | 6.5 | 6.5 |

Infrared absorption:
1630 cm$^{-1}$ (C=N), 1250 cm$^{-1}$ (=C—O), 960 cm$^{-1}$ (O—C—N).

Nuclear magnetic resonance:
1.4 ppm (6H), 3.7 ppm (3H), 4.3 ppm (2H), 6.3–8.6 ppm (15H).

(3) Application

A polyvinyl butyral/butanol solution containing the above compound dissolved therein at a concentration of 0.5% by weight was coated and dried on a glass plate to obtain a polyvinyl butyral coated plate having the above compound incorporated therein. The plate showed a blue color under irradiation with ultraviolet rays, and, when the light was removed and the plate was allowed to stand in the dark, the original colorless state was promptly restored.

EXAMPLE 3

(1) Synthesis of 1-(2-methylbenzyl)-3,3-dimethylspiro[indoline-2,3'-[3H]-naphtho[2,1-b](1,4)-oxazine]

In 100 ml of toluene were dissolved 4.8 g of 2,3,3-trimethylindolenine, 5.6 g of 2-methylbenzyl bromide, 4.7 g of α-nitroso-β-naphthol and 5.0 g of piperidine. Nitrogen gas was bubbled into the solution for 10 minutes and then the solution was refluxed in a nitrogen current for 2 hours. After the reaction, the reaction mixture was concentrated and then column chromatography separation was carried out by using silica gel as a supporting carrier and toluene as a developing solvent. The solvent was removed by distillation and the obtained solid was recrystallized from methanol to obtain a white crystal of 1-(2-methylbenzyl)-3,3-dimethylspiro[indoline-2,3'-[3H]-naphtho[2,1-b](1,4)-oxazine].

(2) Results of analysis

Melting point: 156° C.
Elementary analysis:

|   | Found value (%) | Calculated value (%) |
|---|---|---|
| C | 83.4 | 83.3 |
| H | 6.5 | 6.2 |
| N | 6.5 | 6.7 |

Infrared absorption:
1625 cm$^{-1}$ (C=N), 1253 cm$^{-1}$ (=C—O), 952 cm$^{-1}$ (O—C—N).

Nuclear magnetic resonance:
1.4 ppm (6H), 2.2 ppm (3H), 4.4 ppm (2H), 6.2–8.6 ppm (15H).

(3) Application

A polymethyl methacrylate plate containing the above compound, which was prepared in the same manner as described in Example 1, showed a bluish purple color under irradiation with ultraviolet rays. When the light was removed and the plate was allowed to stand in the dark, the original colorless state was promptly restored.

EXAMPLE 4

(1) Synthesis of 1-(3-methylbenzyl)-3,3-dimethylspiro[indoline-2,3'-[3H]-naphtho[2,1-b](1,4)-oxazine]

In 100 ml of absolute ethanol were dissolved 4.8 g of 2,3,3-trimethylindolenine, 4.7 g of α-nitroso-β-naphthol and 5.0 g of piperidine. Nitrogen gas was bubbled into the solution for 10 minutes and then the solution was refluxed in a nitrogen current for 1 hour. Then, the temperature of the reaction mixture was lowered to 50° C. 5.6 g of 3-methylbenzyl bromide was added to the reaction mixture and the mixture was then refluxed for 2 hours. Purification was carried out in the same manner as described in Example 1 to obtain a white crystal of 1-(3-methylbenzyl)-3,3-dimethylspiro [indoline-2,3'-[3H]-naphtho[2,1-b](1,4)-oxazine].

(2) Results of analysis

Melting point: 150°–151° C.
Elementary analysis:

|   | Found value (%) | Calculated values (%) |
|---|---|---|
| C | 83.5 | 83.3 |
| H | 6.1 | 6.2 |
| N | 6.7 | 6.7 |

Infrared absorption spectrum:
1620 cm$^{-1}$ (C=N), 1250 cm$^{-1}$ (=C—O), 956 cm$^{-1}$ (O—C—N).

Nuclear magnetic resonance:
1.4 ppm (6H), 2.2 ppm (3H), 4.4 ppm (2H), 6.2–8.6 ppm (15H).

(3) Application

A polymethyl methacrylate plate containing the above compound, which was prepared in the same manner as described in Example 1, showed a bluish purple color under irradiation with ultraviolet rays. When the light was removed and the plate was allowed to stand in the dark, the original colorless state was promptly restored.

EXAMPLE 5

(1) Synthesis of 1-(4-methylbenzyl)-3,3-dimethylspiro[indoline-2,3'-[3H]-naphtho[2,1-b](1,4)-oxazine]

Reaction was carried out in the same manner as described in Example 1. The reaction mixture was concentrated and then subjected to column separation by using alumina as a supporting carrier and toluene as a developing solvent. The solvent was removed by distillation and the obtained solid was recrystallized from hexane to obtain a white crystal of 1-(4-methylbenzyl)-3,3-dimethylspiro[indoline-2,3'-[3H]-naphtho[2,1-b](1,4)-oxazine].

(2) Results of analysis

Melting point: 173.5° C.
Elementary analysis:

|   | Found value (%) | Calculated value (%) |
|---|---|---|
| C | 83.2 | 83.3 |
| H | 6.1 | 6.2 |
| N | 6.6 | 6.7 |

Infrared absorption:
1620 cm$^{-1}$ (C=N), 1252 cm$^{-1}$ (=C—O), 958 cm$^{-1}$ (O—C—N).
Nuclear magnetic resonance:
1.4 ppm (6H), 2.3 ppm (3H), 4.3 ppm (2H), 6.3–8.6 ppm (15H).

(3) Application

A polyvinyl butyral coated plate containing the above compound, which was prepared in the same manner as described in Example 2, showed a blue color under irradiation with ultraviolet rays. When the light was removed and the plate was allowed to stand in the dark, the original colorless state was promptly restored.

EXAMPLE 6

(1) Synthesis of 1-(3,5-dimethylbenzyl)-3,3-dimethylspiro[indoline-2,3'-[3H]-naphtho[2,1-b](1,4)-oxazine]

Reaction was carried out in the same manner as described in Example 3. The reaction mixture was concentrated and then subjected to column chromatography separation by using alumina as a supporting carrier and hexane as a developing solvent. The solvent was removed by distillation and the obtained solid was recrystallized from propanol to obtain a white crystal of 1-(3,5-dimethylbenzyl)-3,3-dimethylspiro[indoline-2,3'-[3H]-naphtho[2,1-b](1,4)-oxazine].

(2) Results of analysis

Melting point: 177.5° C.
Elementary analysis:

|   | Found value (%) | Calculated value (%) |
|---|---|---|
| C | 83.2 | 83.3 |
| H | 6.6 | 6.5 |
| N | 6.5 | 6.5 |

Infrared absorption:
1615 cm$^{-1}$ (C=N), 1250 cm$^{-1}$ (=C—O), 962 cm$^{-1}$ (O—C—N).
Nuclear magnetic resonance:
1.4 ppm (6H), 2.2 ppm (6H), 4.4 ppm (2H), 6.2–8.6 ppm (14H).

(3) Application

A silica gel thin layer chromatography plate (Spot Film S-196 supplied by Tokyo Kasei K.K.) in which the above compound was adsorbed showed a dense blue color under irradiation with ultraviolet rays. When the light was removed and the plate was allowed to stand in the dark, the original white color was promptly restored.

EXAMPLE 7

(1) Synthesis of 1-(2,4,6-trimethylbenzyl)-3,3-dimethyspiro[indoline-2,3'-[3H]-naphtho[2,1-b](1,4)-oxazine]

The procedures to the step of obtaining a crude crystal were repeated in the same manner as described in Example 1. The crude crystal was recrystallized from toluene and then from butanol to obtain a white crystal.

(2) Results of analysis

Melting point: 218° C.
Elementary analysis:

|   | Found value (%) | Calculated value (%) |
|---|---|---|
| C | 83.6 | 83.4 |
| H | 6.8 | 6.7 |
| N | 6.2 | 6.3 |

Infrared absorption:
1625 cm$^{-1}$ (C=N), 1253 cm$^{-1}$ (=C—O), 955 cm$^{-1}$ (O—C—N).
Nuclear magnetic resonance:
1.2 ppm (6H), 2.2 ppm (9H), 4.5 ppm (2H), 6.6–8.6 ppm (13H).

(3) Application

An alumina thin layer chromatography plate (Spot Film S-188 supplied by Tokyo Kasei K.K.) in which the above compound was adsorbed showed a blue color under irradiation with ultraviolet rays. When the light was removed and the plate was allowed to stand in the dark, the original colorless state was promptly restored.

EXAMPLE 8

(1) Synthesis of 1-(4-chlorobenzyl)-3,3-dimethylspiro[indoline-2,3'-[3H]-naphtho[2,1-b](1,4)-oxazine]

Reaction and purification were carried out in the same manner as described in Example 4 except that benzene was used as the reaction solvent, whereby a white crystal was obtained.

(2) Results of analysis

Melting point: 188° C.
Elementary analysis:

| | Found value (%) | Calculated value (%) |
|---|---|---|
| C | 76.8 | 76.6 |
| H | 5.1 | 5.2 |
| N | 6.4 | 6.4 |

Infrared absorption:
1620 cm$^{-1}$ (C=N), 1250 cm$^{-1}$ (=C—O), 959 cm$^{-1}$ (O—C—N).
Nuclear magnetic resonance:
1.4 ppm (6H), 4.3 ppm (2H), 6.3–8.6 ppm (15H).

(3) Application

An acetone solution containing the above compound dissolved showed a blue color under irradiation with ultraviolet rays. When the light was removed and the solution was allowed to stand in the dark, the original colorless state was promptly restored.

EXAMPLE 9

(1) Synthesis of 1-(4-bromobenzyl)-3,3-dimethylspiro[indoline-2,3'-[3H]- naphtho[2,1-b](1,4)-oxazine]

Reaction and purification were carried out in the same manner as described in Example 3 except that absolute ethanol was used as the reaction solvent, whereby a white crystal was obtained.

(2) Results of analysis

Melting point: 180°–181° C.
Elementary analysis:

| | Found value (%) | Calculated value (%) |
|---|---|---|
| C | 69.3 | 69.5 |
| H | 4.6 | 4.8 |
| N | 5.7 | 5.8 |

Infrared absorption:
1625 cm$^{-1}$ (C=N), 1251 cm$^{-1}$ (=C—O), 960 cm$^{-1}$ (O—C—N).
Nuclear magnetic resonance:
1.4 ppm (6H), 4.3 ppm (2H), 6.3–8.6 ppm (15H).

(3) Application

A hexane solution containing the above compound dissolved showed a purple color under irradiation with ultraviolet rays. When the light was removed and the solution was allowed to stand in the dark, the original colorless state was promptly restored.

EXAMPLE 10

(1) Synthesis of 1-(2-fluorobenzyl)-3,3-dimethylspiro[indoline-2,3'-[3H]- naphtho[2,1-b](1,4)-oxazine]

Reaction and purification were carried out in the same manner as described in Example 1, whereby a white crystal was obtained.

(2) Results of analysis

Melting point: 154° C.
Elementary analysis:

| | Found value (%) | Calculated value (%) |
|---|---|---|
| C | 79.8 | 79.6 |
| H | 5.2 | 5.5 |
| N | 6.7 | 6.6 |

Infrared absorption:
1620 cm$^{-1}$ (C=N), 1250 cm$^{-1}$ (=C—O), 950 cm$^{-1}$ (O—C—N).
Nuclear magnetic resonance:
1.4 ppm (6H), 4.4 ppm (2H), 6.2–8.6 ppm (15H).

(3) Application

A polymethyl methacrylate plate containing the above compound incorporated therein, which was prepared in the same manner as described in Example 1, showed a bluish purple color under irradiation with ultraviolet rays. When the light was removed and the plate was allowed to stand in the dark, the original colorless state was promptly restored.

EXAMPLE 11

(1) Synthesis of 1-(3-fluorobenzyl)-3,3-dimethylspiro[indoline-2,3'-[3H]- naphtho[2,1-b](1,4)-oxazine]

Reaction and purification were carried out in the same manner as described in Example 4 except that triethylamine was used as the basic substance, whereby a white crystal was obtained.

(2) Results of analysis

Melting point: 182° C.
Elementary analysis:

| | Found value (%) | Calculated value (%) |
|---|---|---|
| C | 79.5 | 79.6 |
| H | 5.3 | 5.5 |
| N | 6.6 | 6.4 |

Infrared absorption:
1625 cm$^{-1}$ (C=N), 1247 cm$^{-1}$ (=C—O), 950 cm$^{-1}$ (O—C—N).
Nuclear magnetic resonance:
1.4 ppm (6H), 4.4 ppm (2H), 6.2–8.6 ppm (15H).

(3) Application

A polymethyl methacrylate plate containing the above compound incorporated therein, which was prepared in the same manner as described in Example 1, showed a bluish purple color under irradiation with ultraviolet rays. When the light was removed and the plate was allowed to stand still in the dark, the original colorless state was restored.

EXAMPLE 12

(1) Synthesis of 1-(4-fluorobenzyl)-3,3-dimethylspiro[indoline-2,3'-[3H]- naphtho[2,1-b](1,4)-oxazine]

Reaction and purification were carried out in the same manner as described in Example 2 except that methyl cellosolve was used as the reaction solvent, whereby a white crystal was obtained.

(2) Results of analysis

Melting point: 194° C.
Elementary analysis:

|   | Found value (%) | Calculated value (%) |
|---|---|---|
| C | 79.6 | 79.6 |
| H | 5.4 | 5.5 |
| N | 6.6 | 6.6 |

Infrared absorption: 1625 cm$^{-1}$ (C=N), 1250 cm$^{-1}$ (=C—O), 960 cm$^{-1}$ (O—C—N).

Nuclear magnetic resonance: 1.4 ppm (6H), 4.4 ppm (2H), 6.2–8.6 ppm (15H).

(3) Application A polyvinyl butyral coated plate containing the above compound incorporated therein, which was prepared in the same manner as described in Example 2, showed a blue color under irradiation with ultraviolet rays. When the light was removed and the plate was allowed to stand in the dark, the original colorless state was promptly restored.

EXAMPLE 13

Synthesis of 1-(2,4-difluorobenzyl)-3,3-dimethylspiro[indoline-2,3'-[3H]-naphtho[2,-1-b](1,4)-oxazine]

The procedures to the step of obtaining a crude crystal were repeated in the same manner as described in Example 1. The crude crystal was recrystallized from hexane and then from ethanol to obtain a white crystal.

(2) Results of analysis

Melting point: 159° C.
Elementary analysis:

|   | Found value (%) | Calculated value (%) |
|---|---|---|
| C | 76.6 | 76.4 |
| H | 4.8 | 5.0 |
| N | 6.3 | 6.4 |

Infrared absorption: 1615 cm$^{-1}$ (C=N), 1248 cm$^{-1}$ (=C—O), 955 cm$^{-1}$ (O—C—N).

Nuclear magnetic resonance: 1.4 ppm (6H), 4.4 ppm (2H), 6.2–8.6 ppm (14H).

(3) Application

A polyvinyl butyral coated plate containing the above compound incorporated therein, which was prepared in the same manner as described in Example 2, showed a blue color under irradiation with ultraviolet rays. When the light was removed and the plate was allowed to stand in the dark, the original colorless state was promptly restored.

EXAMPLE 14

(1) Synthesis of 1-(2,3,4,5,6-pentafluorobenzyl)-3,3-dimethylspiro[indoline-2,3'-[3H]-naphtho [2,1-b](1,4)-oxazine]

The reaction was carried out in the same manner as described in Example 2. The reaction mixture was concentrated and then subjected to column chromatography separation by using silica gel as a supporting carrier and hexane as a developing solvent. The solvent was removed by distillation and then the obtained solid was recrystallized from ethanol to obtain a white crystal.

(2) Results of analysis

Melting point: 126° C.
Elementary analysis:

|   | Found value (%) | Calculated value (%) |
|---|---|---|
| C | 68.0 | 67.5 |
| H | 3.8 | 3.8 |
| N | 5.6 | 5.6 |

Infrared absorption:
1625 cm$^{-1}$ (C=N), 1243 cm$^{-1}$ (=C—O), 955 cm$^{-1}$ (O—C—N).

Nuclear magnetic resonance:
1.4 ppm (6H), 4.4 ppm (2H), 6.2–8.6 ppm (11H).

(3) Application

A polymethyl methacrylate plate containing the above compound incorporated therein, which was prepared in the same manner as described in Example 1, showed a purple color under irradiation with ultraviolet rays. When the light was removed and the plate was allowed to stand in the dark, the original colorless state was promptly restored.

EXAMPLE 15

(1) Synthesis of 1-(4-cyanobenzyl)-3,3-dimethylspiro[indoline-2,3'-[3H]-naphtho[2,1-b](1,4)-oxazine]

Reaction was carried out in the same manner as described in Example 3. The reaction mixture was concentrated and then subjected to column separation by using silica gel as a supporting carrier and chloroform as a developing solvent. The solvent was removed by distillation and then the obtained solid was recrystallized from ethanol to obtain a white crystal.

(2) Results of analysis

Melting point: 184°–185° C.
Elementary analysis:

|   | Found value (%) | Calculated value (%) |
|---|---|---|
| C | 81.2 | 81.1 |
| H | 5.1 | 5.4 |
| N | 9.7 | 9.8 |

Infrared absorption:
2220 cm$^{-1}$ (C≡N), 1626 cm$^{-1}$ (C=N), 1255 cm$^{-1}$ (=C—O), 962 cm$^{-1}$ (O—C—N).

Nuclear magnetic resonance: 1.4 ppm (6H), 4.4 ppm (2H), 6.2–8.6 ppm (15H).

(3) Application

A polymethyl methacrylate plate containing the above compound incorporated therein, which was prepared in the same manner as described in Example 1, showed a bluish purple color under irradiation with ultraviolet rays. When the light was removed and the plate was allowed to stand still in the dark, the original colorless state was promptly restored.

EXAMPLE 16

(1) Synthesis of 1-(4-trifluoromethylbenzyl)-3,3-dimethylspiro[indoline-2,3'-[3H]-naphtho[2,1-b](1,4)-oxazine]

Reaction and purification were carried out in the same manner as described in Example 2, whereby a white crystal was obtained.

(2) Results of analysis

Melting point: 140°–141° C.

Elementary analysis:

|   | Found value (%) | Calculated value (%) |
|---|---|---|
| C | 74.1 | 73.7 |
| H | 4.8 | 4.9 |
| N | 6.2 | 5.9 |

Infrared absorption: 1618 cm$^{-1}$ (C=N), 1325 cm$^{-1}$ (CF$_3$), 1248 cm$^{-1}$ (=C—O), 960 cm$^{-1}$ (O—C—N).

Nuclear magnetic resonance: 1.4 ppm (6H), 4.4 ppm (2H), 6.2–8.6 ppm (15H).

(3) Application

A polymethyl methacrylate plate containing the above compound incorporated therein, which was prepared in the same manner as described in Example 1, showed a purple color. When the light was removed and the plate was allowed to stand in the dark, the original colorless state was promptly restored.

EXAMPLE 17

(1) Synthesis of 1-(4-nitrobenzyl)-3,3-dimethylspiro[indoline-2,3'-[3H]-naphtho[2,1-b](1,4)-)-oxazine]

Reaction and purification were carried out in the same manner as described in Example 1, whereby a white crystal was obtained.

(2) Results of analysis

Melting point: 188°–189° C.
Elementary analysis:

|   | Found value (%) | Calculated value (%) |
|---|---|---|
| C | 75.0 | 74.8 |
| H | 5.0 | 5.1 |
| N | 9.2 | 9.4 |

Infrared absorption: 1620 cm$^{-1}$ (C=N), 1517 cm$^{-1}$ and 1345 cm$^{-1}$ (NO$_2$), 1250 cm$^{-1}$ (=C—O), 945 cm$^{-1}$ (O—C—N).

Nuclear magnetic resonance:
1.4 ppm (6H), 4.4 ppm (2H), 6.2–8.5 ppm (15H).

(3) Application

A polymethyl methacrylate plate containing the above compound incorporated therein, which was prepared in the same manner as described in Example 1, showed a purple color under irradiation with ultraviolet rays. When the light was removed and the plate was allowed to stand in the dark, the original colorless state was promptly restored.

EXAMPLE 18

(1) Synthesis of 1-(2-phenylethyl)-3,3-dimethylspiro[indoline-2,3'-[3H]-naphtho[2,1-b](1,4)-oxazine]

The reaction was carried out in the same manner as described in Example 1. The reaction mixture was concentrated and then subjected to column separation by using alumina as a carrier and toluene as a developing solvent. Furthermore, column separation was carried out by using silica gel as a supporting carrier and toluene as a developing solvent. After removal of the solvent by distillation, the obtained solid was recrystallized from ethanol to obtain a white crystal.

(2) Results of analysis

Melting point: 107° C.
Elementary analysis:

|   | Found value (%) | Calculated value (%) |
|---|---|---|
| C | 83.0 | 83.3 |
| H | 6.2 | 6.2 |
| N | 6.7 | 6.7 |

Infrared absorption: 1620 cm$^{-1}$ (C=N), 1253 cm$^{-1}$ (=C—O), 970 cm$^{-1}$ (O—C—N).

Nuclear magnetic resonance: 1.4 ppm (6H), 2.9 ppm (2H), 3.4 ppm (2H), 6.2–8.6 ppm (16H).

(3) Application

A polyvinyl butyral coated plate containing the above compound incorporated therein, which was prepared in the same manner as described in Example 2, showed a blue color under irradiation with ultraviolet rays. When the light was removed and the plate was allowed to stand in the dark, the original colorless state was promptly restored.

EXAMPLE 19

(1) Synthesis of 1-(3-phenylpropyl)-3,3-dimethylspiro[indoline-2,3'-[3H]-naphtho[2,1-b](1,4)-oxazine]

The reaction and purification were carried out in the same manner as described in Example 18, whereby a white crystal was obtained.

(2) Results of analysis

Melting point: 116° C.
Elementary analysis:

|   | Found value (%) | Calculated value (%) |
|---|---|---|
| C | 83.0 | 83.3 |
| H | 6.6 | 6.5 |
| N | 6.4 | 6.5 |

Infrared absorption: 1625 cm$^{-1}$ (C=N), 1248 cm$^{-1}$ (=C—O), 970 cm$^{-1}$ (O—C—N).

Nuclear magnetic resonance: 1.4 ppm (6H), 2.0 ppm (2H), 2.6 ppm (2H), 6.2–8.6 ppm (16H).

(3) Application

A polyvinyl butyral coated plate containing the above compound incorporated therein, which was prepared in the same manner as described in Example 2, showed a blue color under irradiation with ultraviole rays. When the light was removed and the plate was allowed to stand in the dark, the original colorless state was promptly restored.

EXAMPLE 20

(1) Synthesis of 1-[(2-naphthyl)methyl]-3,3-dimethylspiro[indoline-2,3'-[3H]-naphtho[2,1-b](1,4)-oxazine]

The reaction and purification were carried out in the same manner as described in Example 7, whereby a white crystal was obtained.

(2) Results of analysis

Melting point: 216° C.

Elementary analysis:

|   | Found value (%) | Calculated value (%) |
|---|---|---|
| C | 84.9 | 84.6 |
| H | 5.6 | 5.7 |
| N | 6.2 | 6.2 |

Infrared absorption: 1622 cm$^{-1}$ (C=N), 1255 cm$^{-1}$ (=C—O), 960 cm$^{-1}$ (O—C—N).

Nuclear magnetic resonance: 1.4 ppm (6H), 4.6 ppm (2H), 6.3–8.6 ppm (18H).

(3) Application

A polyvinyl butyral coated plate containing the above compound incorporated therein, which was prepared in the same manner as described in Example 2, showed a blue color under irradiation with ultraviolet rays. When the light was removed and the plate was allowed to stand in the dark the original colorless state was promptly restored.

EXAMPLE 21

(1) Synthesis of 1-(2-phenylethyl)-3,3-dimethylspiro[indoline-2,3'-[3H]-naphtho[2,1-b](1,4)-oxazine]

13.8 g of β-phenylethyl tosylate (tosylate: abbreviation for p-toluene-sulfonate) was dissolved in 50 ml of absolute ethanol. 8.0 g of 2,3,3-trimethylindolenine was dissolved in 30 ml of absolute ethanol. Nitrogen gas was bubbled into each solution for 15 minutes, and the two solutions were mixed together and refluxed in a nitrogen stream for 2 hours. Then, the temperature of the reaction mixture was lowered to 50° C. and 10.0 g of triethylamine was added, and the mixture was stirred for 30 minutes. Then, 8.7 g of α-nitroso-β-naphthol was added and the mixture was refluxed for 2 hours. The reaction mixture was concentrated and then subjected to column separation by using alumina as a supporting carrier and toluene as a developing solvent. Toluene was removed by distillation and the obtained crystal was recrystallized from methanol and then from hexane to obtain 1.0 g of a white crystal of 1-(2-phenylethyl)-3,3-dimethylspiro[indoline-2,3'-[3H]naphtho[2,1-b]-(1,4)-oxazine].

(2) Results of analysis

Melting point: 107° C.
Elementary analysis:

|   | Found value (%) | Calculated value (%) |
|---|---|---|
| C | 83.0 | 83.3 |
| H | 6.2 | 6.2 |
| N | 6.7 | 6.7 |

EXAMPLES 22 through 30 and COMPARATIVE EXAMPLES 1 through 5

(1) Preparation of hydrolysis product of γ-glycidoxypropyltrimethoxysilane

A reaction vessel equipped with a rotor was charged with 141.2 parts of γ-glycidoxypropyltrimethoxysilane. 32.3 parts of a 0.01N aqueous solution of hydrochloric acid maintained at 10° C. was dropped with stirring by a magnetic stirrer. After completion of the dropwise addition, stirring was further continued for 30 minutes to obtain a hydrolysis product.

(2) Preparation of photochromic coating composition

To the hydrolysis product obtained in (1) above was added 5 parts of an aluminum salt of acetylacetone as a curing agent. The curing agent was dissolved by stirring for 30 minutes. Then, 0.4 part of a surface active agent and 83.6 parts of n-propanol were added to the solution to obtain a composition having a solid content of 40%. Then, 2 parts of water was added to 38 parts of the lacquer, and a compound shown in Table 1 was added as the component A in an amount shown in Table 1 to form a coating composition.

(3) Coating and curing

The coating composition was flow-coated on a slide glass as a substrate to be coated, and then heat curing was carried out for 1 hour in a hot air dryer maintained at 80° C. to obtain a photochromic coated molded article. Incidentally, in each case, the thickness of the coating layer was 10 μm.

(4) Test results (a) Evaluation of appearance

The presence or absence of coloration in the heat-cured coating before irradiation was checked.

(b) Photochromic test

The photochromic coated molded article obtained in (3) above was irradiated with rays from a chemical lamp as an exciting light source, and the coloration state was observed with the naked eye.

Each of the cured coating films was rubbed with steel wool #0000 and the degree of scratch was examined. It was found that each coating film had such a high surface hardness that the coating film was not scratched even by strong rubbing. As is apparent from the results of the comparative examples, when a spiropyran compound and an 1-methylspiro-oxazine compound were used, coloration was caused in cured films and the obtained films were much inferior in appearance.

TABLE 1

|  | Photochromic compound Name | Amount (parts) | Test results Appearance | Photochromic test |
|---|---|---|---|---|
| Example 22 | 1-benzyl-3,3-dimethylspiro[indoline-2,3'-[3H]—naphtho[2,1-b] (1,4)-oxazine] | 0.092 | Colorless, transparent | Promptly colored blue |
| Example 23 | 1-(4-methoxybenzyl)-3,3-dimethylspiro[indoline-2,3'-[3H]—naphtho[2,1-b] (1,4)-oxazine] | 0.099 | " | " |
| Example 24 | 1-(4-methylbenzyl)-3,3-dimethylspiro[indoline-2,3'-[3H]—naphtho[2,1-b] (1,4)-oxazine] | 0.095 | " | " |
| Example 25 | 1-(4-bromobenzyl)-3,3-dimethylspiro[indoline-2,3'-[3H]—naphtho[2,1-b] (1,4)-oxazine] | 0.110 | " | " |

TABLE 1-continued

| | Photochromic compound Name | Amount (parts) | Appearance | Photochromic test |
|---|---|---|---|---|
| Example 26 | 1-(2,3,4,5,6-pentafluorobenzyl)-3,3-dimethyl-spiro[indoline-2,3'-[3H]—naphtho[2,1-b] (1,4)-oxazine] | 0.114 | " | " |
| Example 27 | 1-(2,4-difluorobenzyl)-3,3-dimethylspiro[indoline-2,3'-[3H]—naphtho[2,1-b] (1,4)-oxazine] | 0.100 | " | " |
| Example 28 | 1-(4-cyanobenzyl)-3,3-dimethylspiro[indoline-2,3'-[3H]—naphtho[2,1-b] (1,4)-oxazine] | 0.098 | " | " |
| Example 29 | 1-(4-chlorobenzyl)-3,3-dimethylspiro[indoline-2,3'-[3H]—naphtho[2,1-b] (1,4)-oxazine] | 0.100 | " | " |
| Example 30 | 1-(3-methylbenzyl)-3,3-dimethylspiro[indoline-2,3'-[3H]—naphtho[2,1-b] (1,4)-oxazine] | 0.095 | " | " |
| Comparative Example 1 | 1,3,3-trimethylspiro[indoline-2,3'-[3H]—naphtho[2,1-b] (1,4)-oxazine] | 0.075 | Colored purple | Colored bluish purple |
| Comparative Example 2 | 1,3,3-trimethyl-5-chlorospiro[indoline-2,3'-[3H]—naphtho[2,1-b] (1,4)-oxazine] | 0.083 | Colored light blue | " |
| Comparative Example 3 | 1',3',3'-trimethyl-6-nitro-8-methoxyspiro[2H—1-benzopyran-2,2'-indoline] | 0.080 | Colored light yellow | Not colored |
| Comparative Example 4 | 1',3',3'-trimethyl-6,8-dibromospiro[2H—1-benzopyran-2,2'-indoline] | 0.099 | Colored light yellow | " |
| Comparative Example 5 | 1',3',3'-trimethyl-6-nitro-8-methoxy-5'-chloro spiro[2H—1-benzopyran-2,2'-indoline] | 0.088 | Colored yellowish brown | " |

The compound of the present invention is colorless in the normal state irrespective of the kinds of the solvent and matrix polymer. When it is irradiated with ultraviolet rays, it is converted to a compound having an absorption wavelength in the visible ray region. If irradiation with ultraviolet rays is stopped, the original colorless state is promptly restored.

The compound of the present invention is a photochromic compound characterized by a high coloration speed, a high decolorization speed, a high coloration density and a very good fatigue resistance. Moreover, the compound of the present invention has such a thermochromic property that when the compound of the present invention is heated in a solvent or matrix polymer, it is converted to a colorless compound or a compound having an absorption wavelength in the visible ray region. When it is cooled, the original colorless state is promptly restored.

The compound of the present invention exhibits excellent acid resistance, and it can be easily and advantageously added to an organopolysiloxane.

The compound of the present invention can be valuably used for the production of not only various optical lenses but also display glass sheets, window panes and glass sheets for automobiles, other vehicles and airplanes.

We claim:

1. A spiro-oxazine compound represented by the following general formula (A):

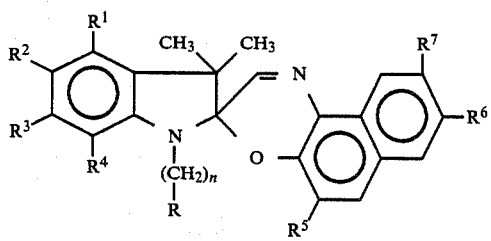

(A)

wherein $R^1$, $R^2$, $R^3$, $R^4$, $R^5$, $R^6$ and $R^7$ independently represent a hydrogen atom or a substituent selected from the group consisting of an alkyl group having 1 or 2 carbon atoms, a halogenated alkyl group having 1 or 2 carbon atoms, an alkoxy group having 1 or 2 carbon atoms, a halogen atom and a nitro group, R represents an unsubstituted or substituted phenyl or naphthyl group, and n is an integer of from 1 to 5.

2. A spiro-oxazine compound according to claim 1, wherein R in the formula (A) represents a phenyl or naphthyl group, which is substituted with at least one member selected from a hydroxyl group, a lower alkoxy group, an amino group, an organic substituted amino group, an aralkoxy group, an aryloxy group, a lower alkyl group, a halogen atom, a cyano group, a carboxyl group, an alkoxycarbonyl group, an acyl group, a trihalomethyl group and a nitro group.

3. A spiro-oxazine compound according to claim 1, wherein R is a phenyl group having a substituent at the meta-position.

4. A spiro-oxazine compound according to claim 1, wherein R is a naphthyl group or a phenyl group having at least two substituents.

5. A spiro-oxazine compound according to claim 1, wherein R has at least one electron-withdrawing substituent.

6. A spiro-oxazine compound according to claim 1, wherein n in the formula (A) is 1.

7. A shaped article comprising an optically transparent material and a spiro-oxazine compound represented by the following general formula (A):

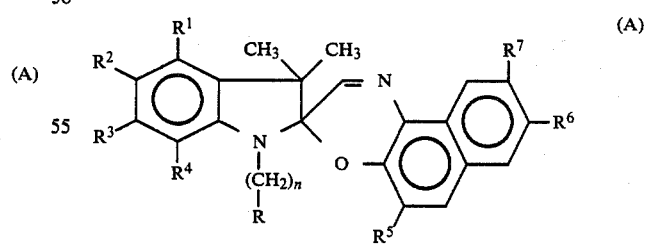

(A)

wherein $R^1$, $R^2$, $R^3$, $R^4$, $R^5$, $R^6$ and $R^7$ independently represent a hydrogen atom or a substituent selected from the group consisting of an alkyl group having 1 or 2 carbon atoms, a halogenated alkyl group having 1 or 2 carbon atoms, an alkoxy group having 1 or 2 carbon atoms, a halogen atom and a nitro group, R represents an unsubstituted or substituted phenyl or naphthyl group, and n is an integer of from 1 to 5.

8. A shaped article according to claim 7, wherein the shaped article is a lens.

9. A shaped article according to claim 7, wherein the spiro-oxazine compound is substantially uniformly contained in the optically transparent material.

10. A shaped article according to claim 7, wherein a coating comprising the spiro-oxazine compound and an optically transparent resin is formed on a shaped article.

11. A shaped article according to claim 10, wherein the optically transparent resin is a polyorganosiloxane.

12. A spiro-oxazine compound according to claim 1 wherein n is greater than 1.

13. A shaped article according to claim 7 wherein n is greater than 1.

* * * * *

UNITED STATES PATENT AND TRADEMARK OFFICE
CERTIFICATE OF CORRECTION

PATENT NO.  : 4,784,474
DATED       : Nov. 15, 1988
INVENTOR(S) : Shinichi Yamamoto
              Takashi Taniguchi It is certified that error appears in the above-identified patent and that said Letters Patent is hereby corrected as shown below:

Column 7, line 28, delete "[3".
  Line should read --
    1-(4-phenylbutyl)-3,3-dimethyl derivative Column 11, Second figure, right side formula should read--
    $X^-$ or $(SO_2R)$    delete "O"

Signed and Sealed this

Twelfth Day of July, 1994

Attest:

BRUCE LEHMAN

*Attesting Officer*        *Commissioner of Patents and Trademarks*